United States Patent [19]

Nicholas

[11] Patent Number: 5,425,743

[45] Date of Patent: * Jun. 20, 1995

[54] SURGICAL INSTRUMENT LOCKING MECHANISM

[75] Inventor: David A. Nicholas, Trumbull, Conn.

[73] Assignee: United States Surgical Corporation, Norwalk, Conn.

[*] Notice: The portion of the term of this patent subsequent to May 24, 2011 has been disclaimed.

[21] Appl. No.: 138,692

[22] Filed: Oct. 19, 1993

Related U.S. Application Data

[63] Continuation of Ser. No. 863,951, Apr. 6, 1992, Pat. No. 5,314,424.

[51] Int. Cl.⁶ ............................................. A61B 17/00
[52] U.S. Cl. .................................. 606/208; 606/205; 606/151; 81/331
[58] Field of Search ............... 606/120, 139, 142, 143, 606/148, 151, 205, 206, 208; 227/19, 182; 81/331

[56] References Cited

U.S. PATENT DOCUMENTS

| | | |
|---|---|---|
| Re. 32,214 | 7/1986 | Schramm . |
| 804,229 | 11/1905 | Hutchinson . |
| 1,452,373 | 4/1923 | Gomez . |
| 1,659,112 | 2/1928 | Littlejohn . |
| 2,363,334 | 11/1944 | Jones . |
| 2,518,994 | 8/1950 | Miller ............... 606/205 |
| 3,807,406 | 4/1974 | Rafferty et al. . |
| 3,964,468 | 6/1976 | Schulz . |
| 4,049,002 | 9/1977 | Kletschka et al. . |
| 4,428,374 | 1/1984 | Auburn . |
| 4,572,185 | 2/1986 | Rich . |
| 4,589,870 | 5/1986 | Citrin et al. . |
| 4,611,595 | 9/1986 | Klieman et al. . |
| 4,614,187 | 9/1986 | Mulhollan et al. . |
| 4,616,650 | 10/1986 | Green et al. . |
| 4,643,190 | 2/1987 | Heimberger . |
| 4,662,371 | 5/1987 | Whipple et al. . |
| 4,671,278 | 6/1987 | Chin . |
| 4,712,545 | 12/1987 | Honkanen . |
| 4,896,661 | 1/1990 | Bogert et al. . |
| 4,935,027 | 6/1990 | Yoon . |
| 4,994,741 | 7/1990 | Hasson ............... 606/206 |
| 5,009,661 | 4/1991 | Michelson . |
| 5,026,370 | 6/1991 | Lottick . |
| 5,031,814 | 7/1991 | Tompkins et al. . |
| 5,085,661 | 2/1992 | Moss . |
| 5,147,357 | 9/1992 | Rose et al. . |
| 5,171,257 | 12/1992 | Ferzli ............... 606/205 |
| 5,176,700 | 1/1993 | Brown et al. ............... 606/206 |
| 5,176,702 | 1/1993 | Bales et al. . |
| 5,205,459 | 4/1993 | Brinkerhoff et al. ............... 227/19 |
| 5,242,456 | 9/1993 | Nash et al. ............... 606/151 |
| 5,286,255 | 2/1994 | Weber ............... 606/208 |
| 5,293,878 | 3/1994 | Bales et al. ............... 606/205 |

FOREIGN PATENT DOCUMENTS

| | | |
|---|---|---|
| 0392547 | 10/1990 | European Pat. Off. . |
| 0392548 | 10/1990 | European Pat. Off. . |
| 836545 | 4/1952 | Germany ............... 606/208 |
| 220437 | 4/1961 | Germany . |
| 1544414 | 2/1990 | U.S.S.R. . |

OTHER PUBLICATIONS

Padgett Instruments Bulletin, Jun. 1, 1976.

*Primary Examiner*—Peter A. Aschenbrenner
*Assistant Examiner*—Jeffrey A. Schmidt

[57] ABSTRACT

An endoscopic or laparoscopic surgical instrument having an internally disposed locking mechanism located within a barrel portion of a handle assembly. The instrument includes a handle assembly having a pivoting handle and a stationary handle, a barrel portion to which an elongated body assembly is secured, and a locking mechanism for releasably positioning a tool mechanism located at the distal end of the body assembly. In one embodiment the locking mechanism comprises a trigger, a brake and a latch spring. In another embodiment the locking mechanism comprises a latch spring and a locking block. A rotational knob and locking member may also be provided to position the body assembly at various orientations to the longitudinal axis.

23 Claims, 12 Drawing Sheets

SURGICAL INSTRUMENT LOCKING MECHANISM

This is a continuation of application Ser. No. 07/863,951 filed Apr. 6, 1992 now U.S. Pat. No. 5,314,424.

BACKGROUND OF THE INVENTION

1. Field of the Invention

The present invention relates to surgical instruments, and more particularly relates to a handle for an endoscopic or laparoscopic surgical instrument having a novel locking mechanism which is internally disposed within the handle to provide for incremental positioning of the jaw members of a surgical instrument in relation to each other. The positioning and subsequent release of the jaw members is accomplished through the provision of a trigger mechanism disposed within the handle.

2. Discussion of the Prior Art

In the prior art, various endoscopic surgical instruments are disclosed which utilize generally complex mechanisms for opening and closing handle members which actuate jaw members to facilitate use of the device at a surgical site. Many devices provide an intricate construction in which a linkage mechanism for opening and closing the jaws requires numerous moving parts, while a sliding arrangement is provided between two extended rod members to activate the linkage mechanism in response to movement of the handle members. In addition, pivoting of the handle members in many cases causes an unwanted radial torquing force on the rod which requires additional space to be provided in the handle members to accommodate the deflected radial movement of the rod.

Furthermore, it is often necessary for the surgeon, or an assistant, to maintain a constant force on the handles to keep the jaw mechanism closed in the event that the instrument is a grasping or gripping device such as forceps, needle holders, or retractors. This limits the surgeon's range, and in the case of an assistant, often requires additional personnel to be present in the operating room, thus restricting movement in an already confining location. To alleviate this problem, it has been known to provide locking mechanisms on the handles of the surgical instruments which allow the surgeon to lock or clamp the jaw members in place to free his hands to operate additional instruments during the course of the operation. Furthermore, this frees the surgical assistant to support the surgeon and eliminates the need for additional assistants. Typical locking devices include arm members which extend between the handles so that a series of ridges or fibs on each arm member engage corresponding ridges on the opposite arm to lock the handles in position. Bending one arm in relation to the other releases the locking mechanism.

A disadvantage associated with these devices concerns the release of the locking mechanism for subsequent movement of the jaw members to remove or reposition the instrument. Generally, the arm members of locking mechanisms are constructed of a resilient material, such as stainless steel or rigid plastic, and the locking forces which hold the arm members in engagement are generated by the natural flexing and biasing of the material of which the arm members are constructed. To release the locking mechanism, the arms must be disengaged by overcoming the locking forces of the arms. Typically, this is accomplished by manually flexing the arms away from each other, necessitating the use of two hands, one to grasp the instrument, and the other to forcibly move the arm members. This, of course, requires the surgeon (or assistant) to cease what he is doing and release the mechanism, thus reducing the effectiveness of the surgeon during the operation, particularly in an emergency situation.

Finally, locking mechanisms located on the handles require special care in sterilization, packaging and storage, as well as in normal handling in the operation room. Dirt and debris may clog the fibs of the locking mechanism thus reducing its effectiveness, and damage to the fibs during storage or packaging may destroy the ribs, rendering the locking mechanism useless.

U.S. Pat. No. 1,452,373, to Gomez discloses a typical locking mechanism for a surgical instrument, in which a plurality of ribs are provided on an extension of the handle member which engage a similar fib member on the opposite handle. Once engaged, the handles must be moved away from each other perpendicular to their longitudinal axis to disengage the locking mechanism to release the jaw mechanism.

U.S. Pat. No. 4,896,661, to Bogerr et al. discloses a surgical instrument having a ratchet mechanism positioned on the handle members which includes a curved rack member attached to one handle member which passes through a slot in the other handle member. A releasable pawl member is provided on the second handle to engage the rack member and provide a means for releasing the ratchet.

U.S. Pat. No. 4,935,027, to Yoon discloses a surgical instrument having a ratchet mechanism positioned between the handle members. A rack member is provided which extends from one handle and passes through a slot in the second handle to lock the handles in place. Pivoting the rack member away from corresponding grooves in the slot will release the ratchet mechanism.

U.S. Pat. No. 4,428,374, to Auburn discloses a surgical instrument having means for positioning and holding the handle members in relation to each other. A rack member is provided on one handle member which extends through a slot in the second handle member in which a releasable pawl mechanism is provided to engage and disengage the rack member.

The novel surgical instrument pursuant to the present invention obviates the disadvantages encountered in the prior art and provides a precise instrument which is easy to manufacture and efficient to use, which eliminates the need for a external locking device and provides for one hand operation of the surgical instrument through manipulation of the opposing handles and a trigger mechanism. The instrument of the present invention incorporates many features which are of use to the surgeon during an operation, including a means for rotating the jaws in relation to the handle if desired, while maintaining a lightweight construction in an easy to handle device in which all of the features may be operated with one hand. Furthermore, the features are positioned so as to provide a maximum line of sight for the surgeon without obstructing the view to the surgical site.

SUMMARY OF THE INVENTION

The present invention provides a novel endoscopic or laparoscopic surgical device which incorporates many features necessary for endoscopic or laparoscopic surgical procedures, and provides a lightweight and easy to use device which may be operated with one hand. The device includes an internal locking mechanism located preferably within the handle mechanism which provides for the locking of the jaws of the instrument in any position necessary for performing the surgical procedure. The locking mechanism is activated by and deactivated by a trigger member situated on the handle assembly by pulling on the trigger member. The device is simple to manufacture, and may incorporate any one of a series of jaw mechanisms for various surgical procedures. The device is a high precision instrument in which many moving parts normally associated with such a device are eliminated, thus reducing instances of mechanical failure requiting expensive repair or ultimate destruction of the instrument.

The endoscopic or laparoscopic surgical instrument employing the locking mechanism of the present invention essentially comprises of a handle assembly, and elongated body assembly, a tool mechanism at an end of the body assembly remote from the handle assembly, and the locking mechanism and associated trigger member within the barrel portion of the handle assembly. The trigger extends out of the barrel portion of the handle assembly adjacent the pivoting and the stationary handle portions of the handle assembly. The body assembly consists of an outer tubular member and an inner rod member which coaxially passes within the outer tubular member. The rod member is attached to the pivoting handle, through the provision of a rotatable connecting means on the pivoting handle. As the handle moves, the connecting means rotates to allow the inner rod to move longitudinally in the outer tube with minimal radial deflection, thereby allowing for the reduction of the required internal spacing between the outer tube and inner rod to result in a more compact and streamlined instrument. Furthermore, unwanted torquing forces are eliminated at the connecting means thus minimizing the possibility of mechanical breakdown of the instrument at the connection between the pivoting handle and the movable inner rod. The tubular member is secured in a conventional manner to the barrel portion which extends into the stationary handle. As the pivoting handle moves, the rod member slidably reciprocates within the outer tube member.

Attached to a distal end of the body assembly is the tool mechanism which opens and closes in response to movement of the pivoting handle in relation to the stationary handle. The tool mechanism may comprise a pair of jaw members wherein one or both jaw members open and close to perform various endoscopic or laparoscopic surgical procedures. The jaw mechanism includes, but is not limited to, a scissors device, a dissecting device, a grasping device, a retractor device, and like mechanisms.

The present invention provides a locking mechanism in the form of a trigger to arrest movement of the inner rod to incrementally position the jaws in relation to each other. The locking mechanism is provided on the barrel portion of the handle assembly and is positioned so that the surgeon may activate the lock mechanism with a single hand. Preferably, the trigger moves linearly to minimize the required spacing within the handle.

Alternately, the locking mechanism of the present invention provides a trigger mechanism which may be operable by a pivoting motion of the trigger as opposed to a linear motion of the trigger. In a further embodiment, the locking mechanism is entirely internal, such that the trigger itself is eliminated.

The present invention also includes the provision of a rotatable knob on the outer tubular member to allow the body assembly and jaw mechanism to rotate to position the jaws at desired angles to the longitudinal axis during the surgical procedure. Preferably, the rotatable knob is secured to the outer tube and positioned in a slot which passes through the barrel portion of the stationary handle, so that a surgeon may rotate the knob, and consequently the body assembly and jaw mechanism, through the use of his thumb while he is holding the stationary handle with his fingers. This frees the surgeon's other hand to simultaneously operate another instrument during surgery.

The present invention may also feature a connection port to provide the device with electrocautery capabilities. A connection port allows for the connection of a suitable jack member to be inserted into the device. The outer tube of the body assembly is provided with electrical insulation, such as heat shrink tubing, which extends a substantial portion of the length of the outer tube. In this embodiment, the handle is molded of plastic material to provide electrical insulation for the user.

In the preferred embodiment, all the above features are incorporated into a single endoscopic and laparoscopic surgical instrument, so that the instrument has electrocautery, rotational, and locking capabilities. However, the instrument of the present invention is constructed with at least the locking capabilities to provide for the locking and unlocking of the surgical instrument during a surgical procedure.

BRIEF DESCRIPTION OF THE DRAWINGS

The foregoing objects and other features of the invention will become more readily apparent and may be understood by referring to the following detailed description of illustrative .embodiments of the endoscopic or laparoscopic surgical instruments having an internal locking mechanism, taken in conjunction with the accompanying drawings, in which.

DETAILED DESCRIPTION OF THE PREFERRED EMBODIMENTS

Figure 1:
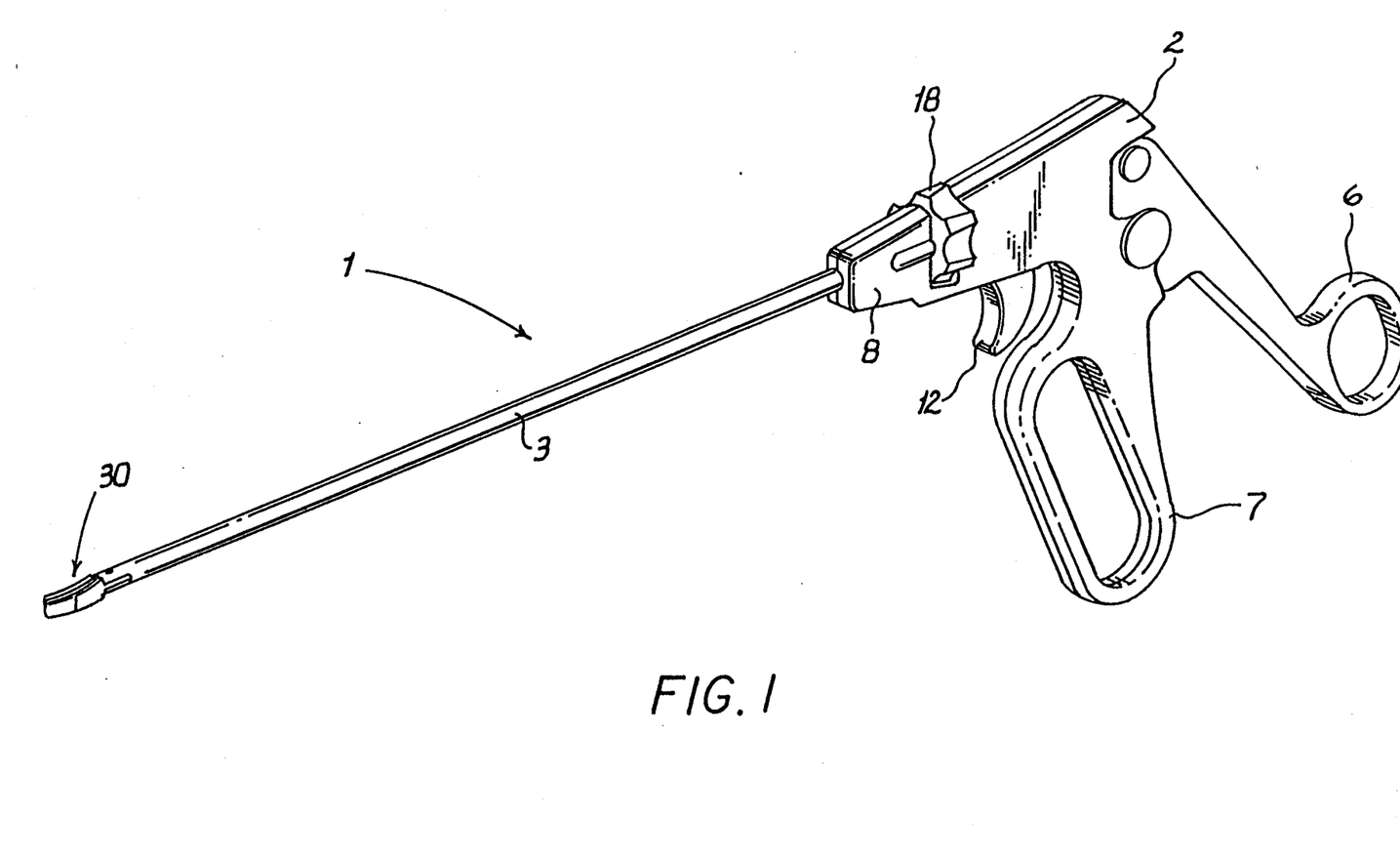
FIG. 1 illustrates a perspective view of a first embodiment of an endoscopic or laparoscopic surgical instrument incorporating a locking mechanism of the present invention.

Referring now in specific detail to the drawings, in which like reference numerals identify similar or identical elements, FIG. 1 illustrates a first embodiment of the endoscopic or laparoscopic surgical instrument 1. In its simplest form, device 1 comprises a handle assembly 2, a body assembly 3, a trigger 12, and an internal locking mechanism assembly (not shown) associated with trigger 12. Handle assembly 2 comprises a pivoting handle 6 and a stationary handle 7 having a barrel portion 8. Body assembly 3 essentially comprises an outer tubular member 22 through which an inner rod member 21 coaxially passes in a slidable arrangement. Outer tube member 22 is secured to barrel portion 8 and remains stationary during operation of the device, so that upon movement of pivoting handle 6, the inner rod 21 reciprocates within tube member 22 to operate a tool mechanism 30 provided at the distal end of the instrument 1. Tool mechanism 30 may comprise any surgical implement, such as scissors device, a grasping device, a forceps device, a retractor device and like mechanisms. Connecting means 9 connects the inner tube member 22 with the pivoting handle 6. Connecting means 9 also provides a rotatable connection means for inner rod 21 during its reciprocating movement within outer tubular member 22, to limit or minimize radial deflection of rod 21 during movement. A rotation knob 18 may be provided which rotates body assembly 3 to orient tool mechanism 30 at various angles to the longitudinal axis.

Figure 2:
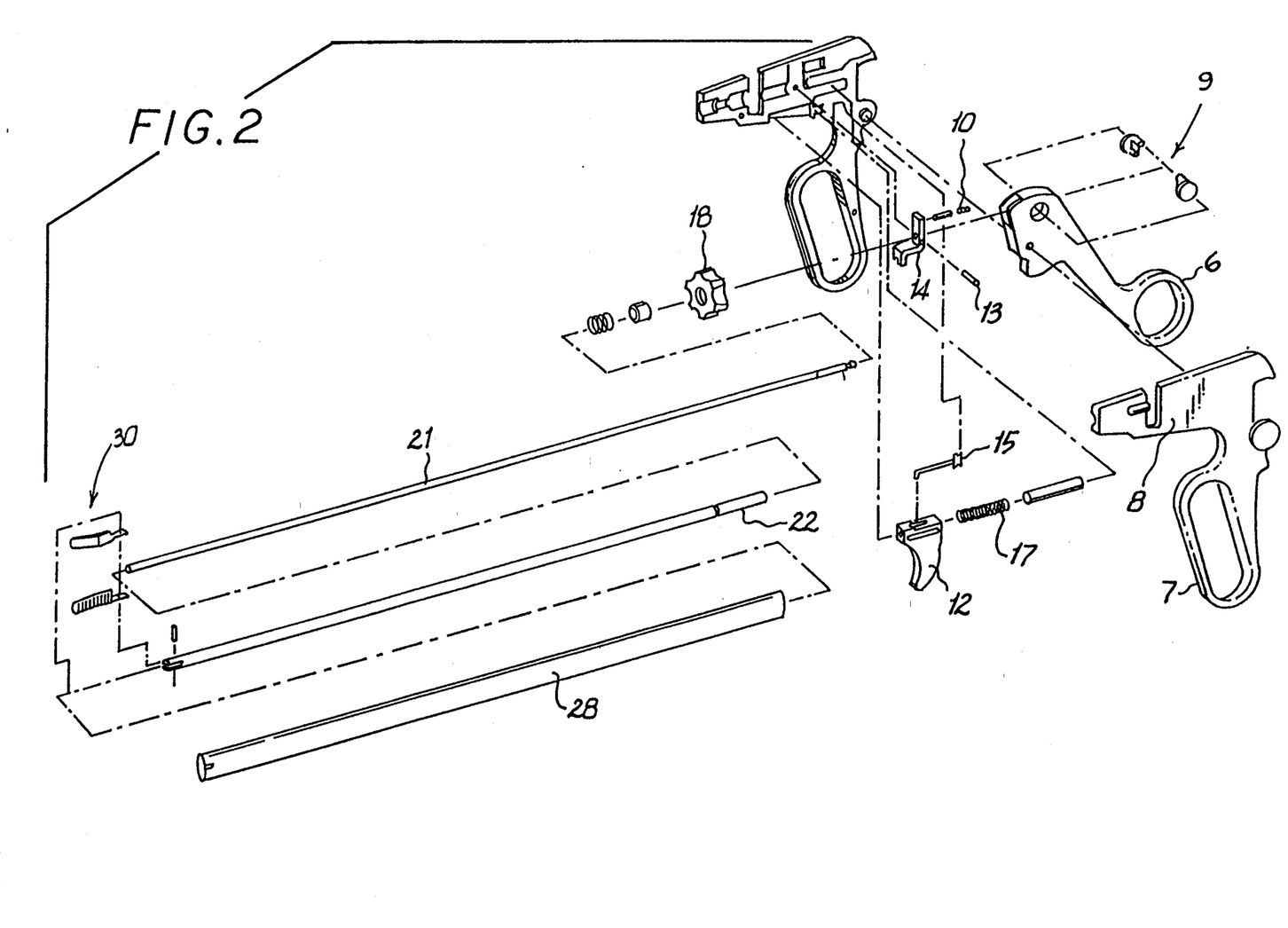
FIG. 2 illustrates an exploded perspective view of the instrument of FIG. 1 showing in detail the locking mechanism according to the present invention.
Figure 3:
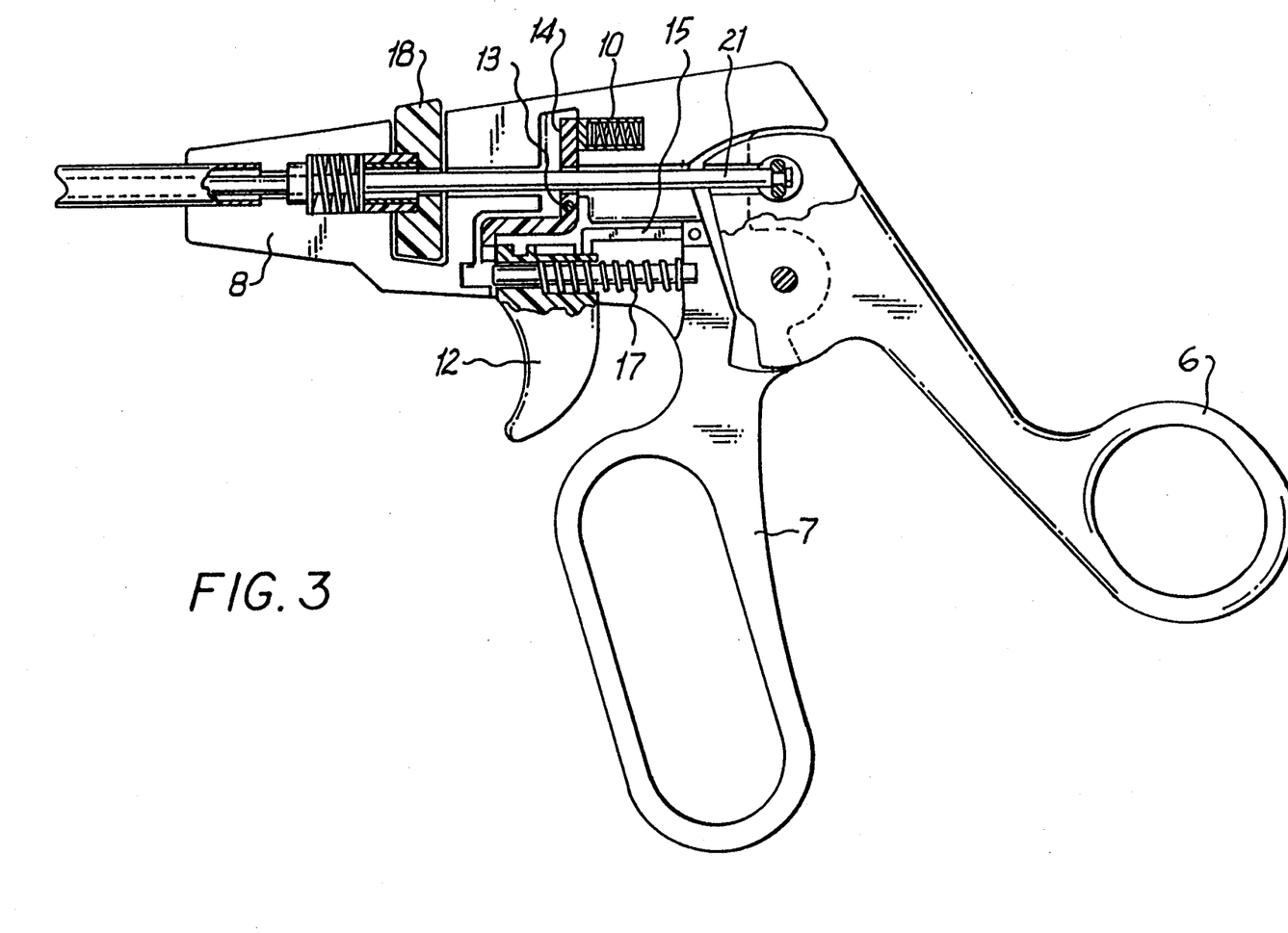
FIG. 3 illustrates a side plan cut-away view of the handle assembly containing the locking mechanism of the embodiment of FIG. 1.

As best seen in FIGS. 2 and 3, the locking mechanism assembly provides for retaining the jaw mechanism 30 of the surgical instrument in various positions by pulling on trigger 12 in a direction toward the handle, or proximal, end of the instrument. Trigger 12 provides a simple and effective means of locking and unlocking the jaw mechanism 30 of the surgical instrument during a surgical procedure using only one hand. The locking mechanism assembly, except for the lower portion of trigger 12, is positioned internally within barrel portion 8 and stationary handle 7 so that none of the mechanism is exposed to environmental conditions.

The locking mechanism assembly includes a trigger 12, a brake 14 which is adapted to pivot with respect to pin 13, and biasing spring 10 which is adapted to bias brake 14 towards the tool mechanism, or distal end, of the instrument 1. Trigger 12 and biasing spring 17 bias the locking mechanism to the unlatched position, and operate in association with latch release spring 15, whose function will be described below.

In use, the surgeon will decide whether or not the distal jaws should lock in a closed configuration upon tissue. If not, trigger 12 remains in its distal, rest position and the jaws freely open and close upon manual operation of pivotal handle 6. Conversely, if the surgeon desires that the jaws should lock, the surgeon draws trigger 12 proximally with his finger. In the embodiment shown in FIGS. 1-3, trigger 12 is moved linearly in a plane parallel to the inner rod 21 and the longitudinal axis of the instrument 1. This proximal movement of trigger 12 allows brake 14 to pivot in a distal direction under the influence of spring 10 such that the aperture 24 (See FIG. 12) in the upwardly extending portion of brake 14 becomes eccentric with respect to center rod 21 which passes therethrough. This eccentricity causes rod 21 to be frictionally retained with respect to distal motion of rod 21. However, rotation of pivotal handle 6 towards stationary handle 7, which translates to proximal motion of center rod 21, is unencumbered since the brake 14 has freedom of motion in the proximal direction, as against compression spring 10. In this manner, the position of the jaws may be adjusted incrementally. Since the spring force of spring 17 is greater than the spring force of spring 10, retention of rod 21 results in locking of the jaws 30 only when latch spring 15 engages recess 42 of cam member 40 which is integral to trigger 12. (See FIG. 4).

Figure 4A:
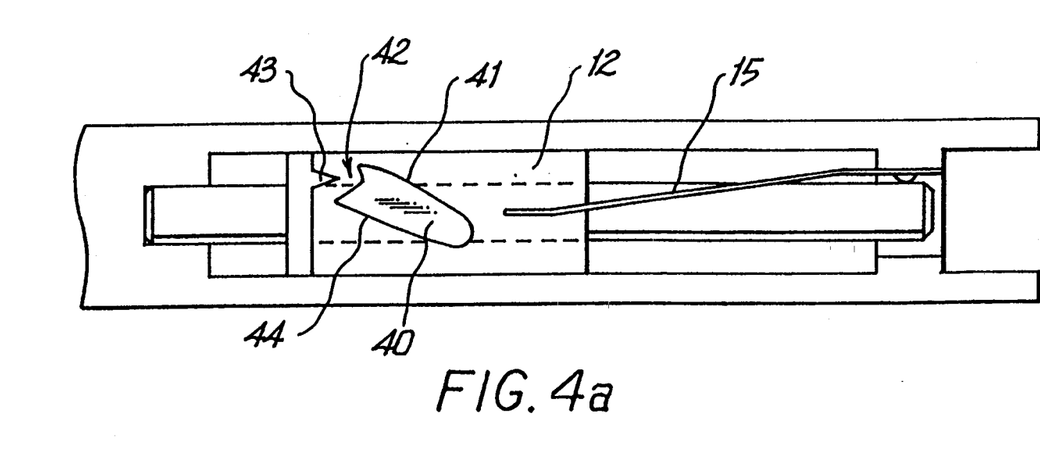
FIGS. 4a–4e illustrate a top plan view of the trigger and latch release spring of the embodiment of FIG. 1 in operation from activation through release of the locking mechanism.
Figure 4B:
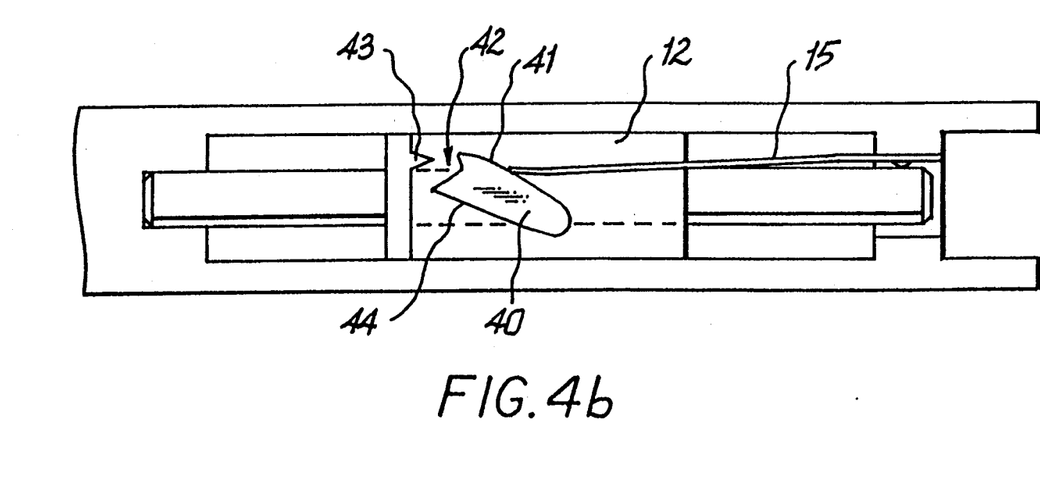
Figure 4C:
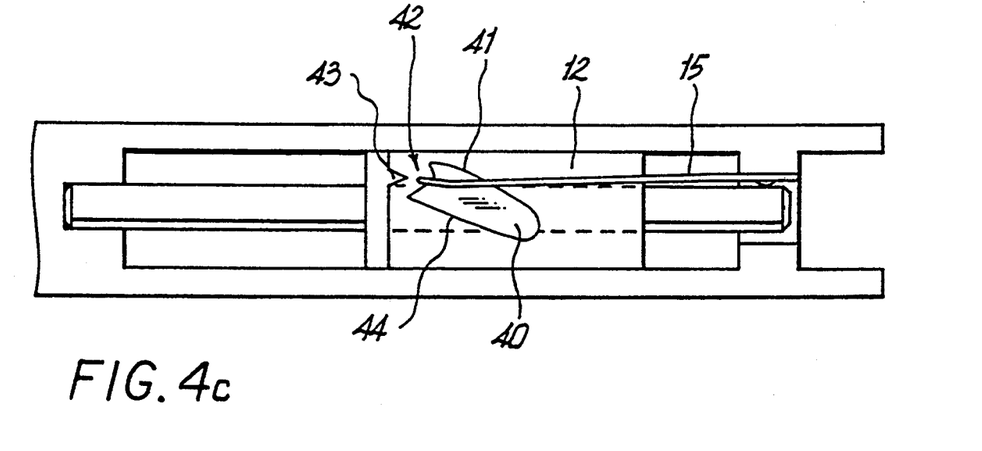

Turning to FIGS. 4a-4e, the operation of latch release spring 15 is illustrated wherein latch spring 15 is adapted to ride against the upwardly projecting diagonal cam member 40 on trigger 12. As seen in FIGS. 4a-4c, trigger 12 moves proximally so that latch release spring 15 rides along cam surface 41 until the distal end of the cam surface is reached, at which point the spring bias of the latch release spring 15 brings latch release spring 15 into a locking engagement within triangular recess 42 cut into the cam member 40 on trigger 12. It is this engagement of latch release spring 15 with the triangular recess 42 on trigger 12 that maintains the trigger in its proximal position and allows the jaws to lock because, as noted above, this proximal movement of trigger 12 allows brake 14 to pivot distally to engage aperture 24 with rod 21 under the bias of compression spring 10.

Figure 4D:
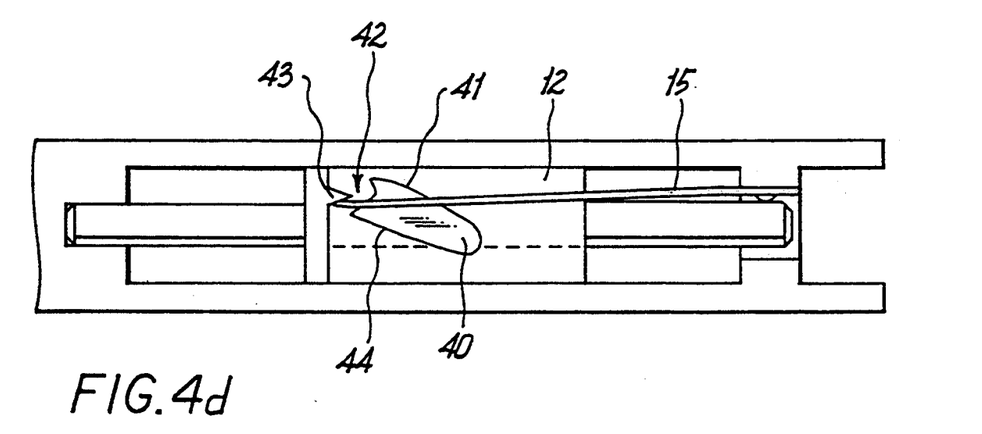
Figure 4E:
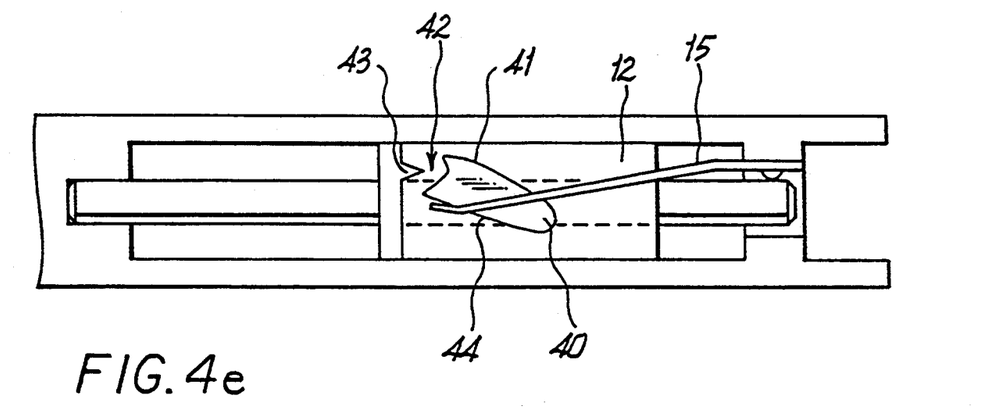

When the surgeon wishes to unlock the gripping jaws, he pulls trigger 12 further in the proximal direction. This proximal movement causes latch release spring 15 to contact triangular release 43 cam at the front edge of trigger 12, as seen in FIG. 4d. This moves the latch release spring 15 over cam member 40, and allows it to then ride on cam surface 44 on the opposite side of the cam member 40 (see FIG. 4e) when the surgeon releases his finger from trigger 12. Thus, trigger 12 is allowed to move distally under the bias of compression spring 17, thereby moving brake 14 in a proximal direction such that the aperture 24 becomes concentrically aligned with center rod 21.

Figure 5:
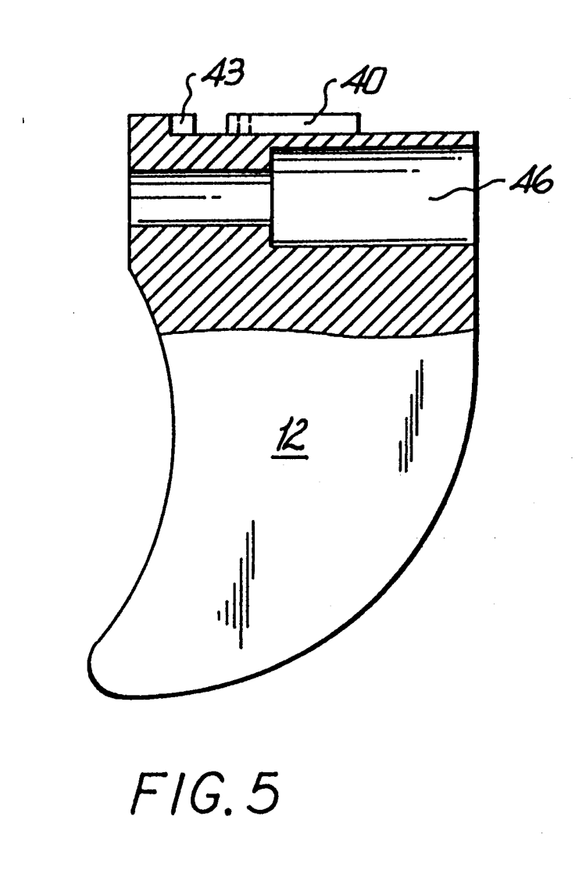
FIG. 5 illustrates a side plan view and partial cut-away view of the trigger of the embodiment of FIG. 1.

FIG. 5 illustrates the trigger 12 of one embodiment of the invention showing the location of diagonal cam member 40 and triangular release cam 43. Also shown is the cavity 46 for compression spring 17 (not shown).

Figure 6:
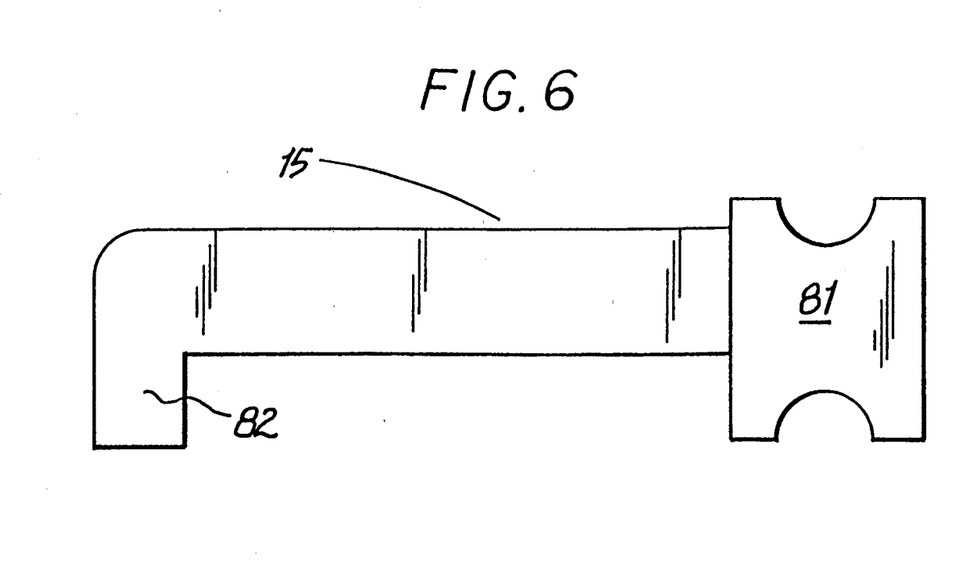
FIG. 6 illustrates a side plan view of the latch release spring of the present invention.

FIG. 6 illustrates a side view of one embodiment of the latch release spring 15. FIG. 6 further illustrates mounting plate 81 and latch release spring finger 82.

Figure 7:
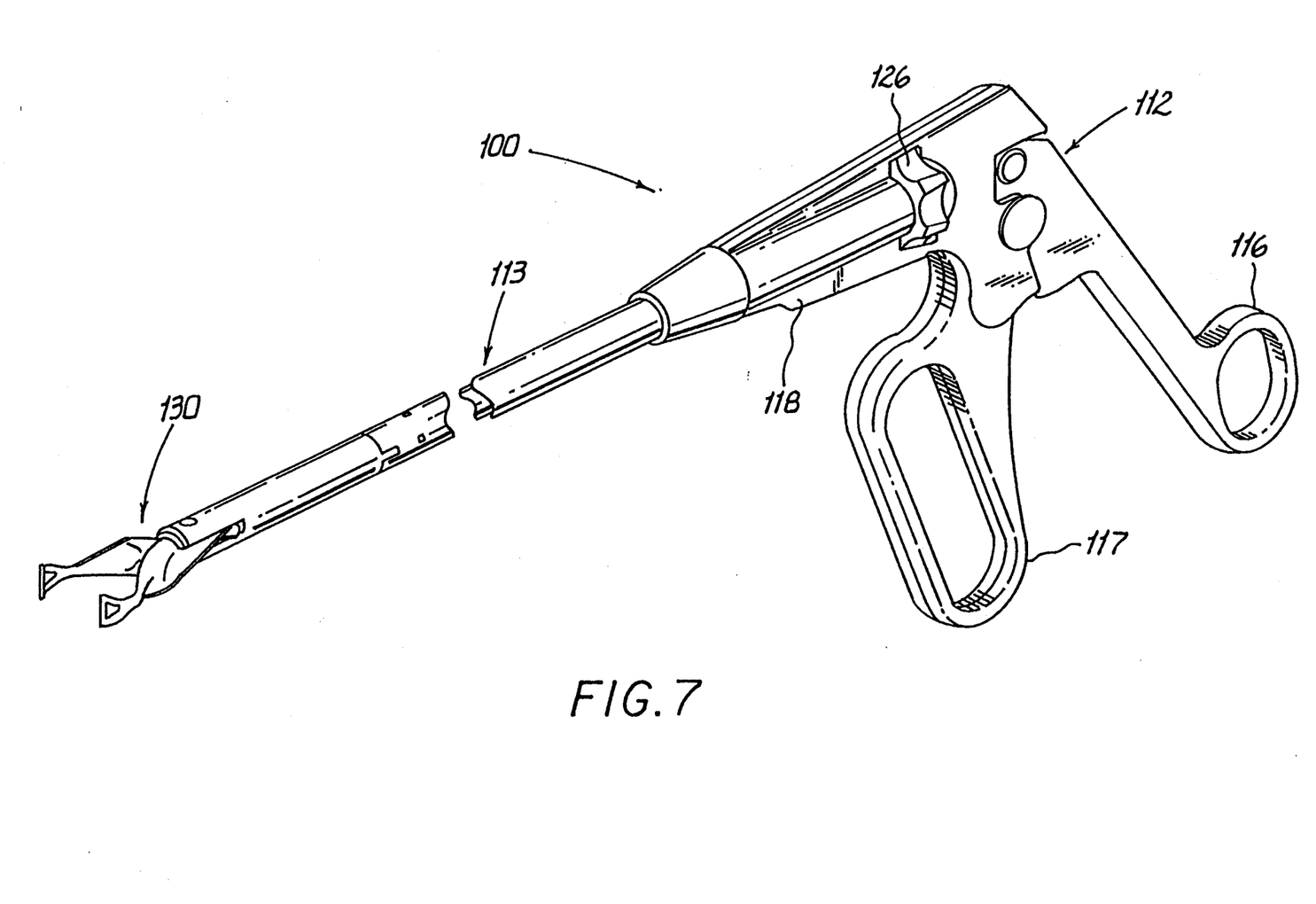
FIG. 7 illustrates a perspective view of an endoscopic or laparoscopic surgical instrument possessing the locking mechanism according to a second embodiment of the present invention.

FIG. 7 illustrates another embodiment of the endoscopic or laparoscopic surgical instrument 100, which is identical to the embodiment of FIG. 1 except that trigger 12 is eliminated and a different tool mechanism is illustrated. In this embodiment, the locking mechanism is incorporated internally within the handle assembly and the body assembly, and not as an independent mechanism as in the embodiment of FIG. 1, to allow for the locking mechanism to lock the surgical instrument only in a fully closed position. Upon movement of pivoting handle 116, the inner rod assembly 121 reciprocates within outer tube assembly 119 to operate a tool mechanism 130 provided at the distal end of the instrument 100. This tool mechanism 130 may comprise any surgical implement, such as a scissors device, a grasper device, a forceps device, a retractor device and like device mechanisms. A rotation knob 126 may be provided which rotates body assembly 113 to orient the tool mechanism at various angles to the longitudinal axis.

In use, when the surgeon desires that the jaws should lock, the surgeon draws pivoting handle 116 toward stationary handle 117 with his thumb. This movement of pivoting handle 116 allows latch release spring 140 to lock in triangular recess 152 of cam member 150 on locking block 141.

Turning to the operation of latch release spring 140, as best seen in FIGS. 9a–9e, this spring is adapted to ride against diagonal cam surface 151 on locking block 141. As locking block 141 moves proximally, latch release spring 140 pivots into locking engagement within a triangular recess 152 of member 150 on locking block 141. It is this engagement of latch release spring 140 with the triangular recess 152 on locking block 141 that maintains the pivoting handle and the jaw mechanism in the locked position.

When the surgeon wishes to unlock the gripping jaws, he squeezes pivoting handle 116 further which causes latch release spring 140 to contact a triangular release cam 153 at the front edge of locking block 141. Inner rod 121 is preferably constructed as a two-piece member as shown. Rod 121a is secured to rod 121b by pin 160 which rides in slot 162, which allows rod 121b to be further drawn proximally even though the jaws of tool mechanism are fully closed. This also serves as a safety mechanism to prevent damage to the tissue positioned between the jaw members. As the surgeon squeezes the handles together, latch release spring 140 pivots to allow it to then ride on the opposite side 154 of the cam member 150 when the surgeon releases pressure from pivoting handle 116. Thus, locking block 141 is allowed to move distally under the bias of spring 142.

FIGS. 9a–9e illustrate the bottom of locking block 141 including diagonal cam member 150 having cam surface 151, triangular recess 152, release cam surface 154, and triangular release cam 153. FIGS. 9a–9e show block 141 operating in a manner identical to that shown in FIGS. 4a–4e, where spring 140 moves along surface 151 into engagement with recess 152 to lock the jaws. To release the block 141, the surgeon further pulls on pivoting handle 116 to engage spring 140 with cam 153, which allows spring 140 to ride along surface 154 until block 141 is fully disengaged.

Figure 8:
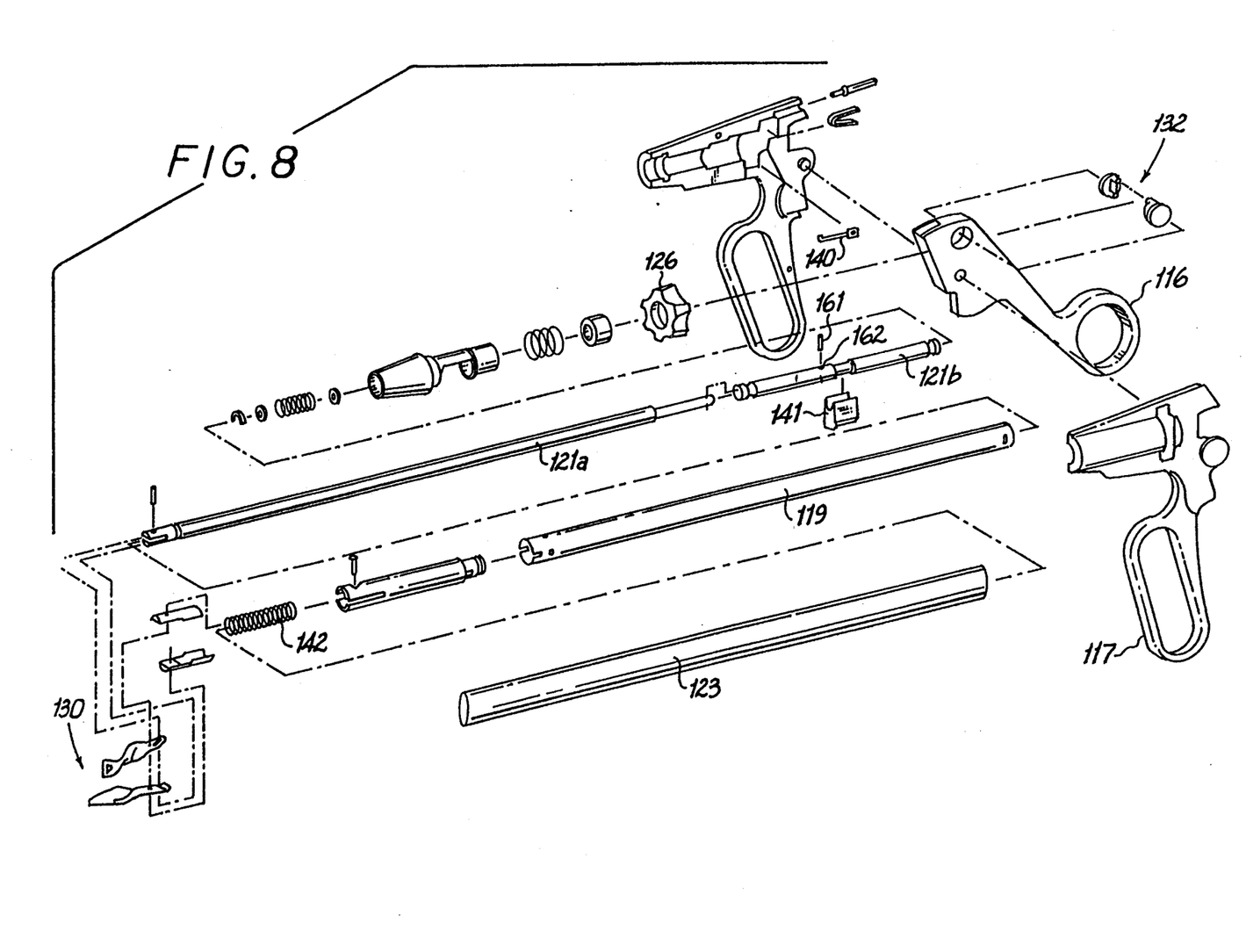
FIG. 8 illustrates an exploded perspective view of the instrument of FIG. 7 showing in detail a second embodiment of the locking mechanism according to the present invention.
Figure 9A:
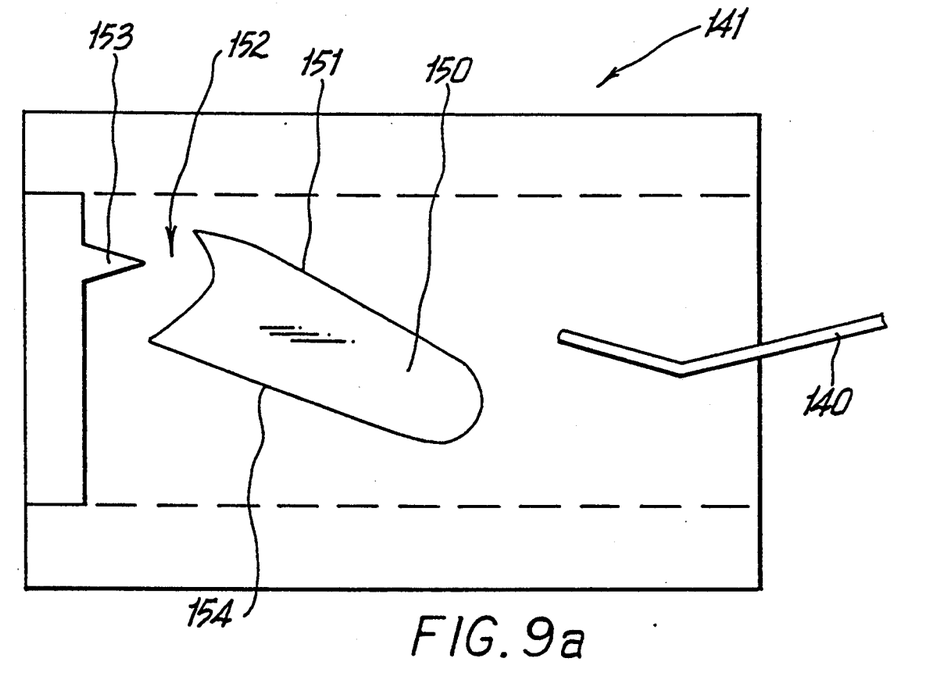
FIGS. 9a-9e illustrate a bottom plan view of the locking mechanism and release spring of the embodiment shown in FIG. 8 in operation from activation through release of the locking mechanism.
Figure 9B:
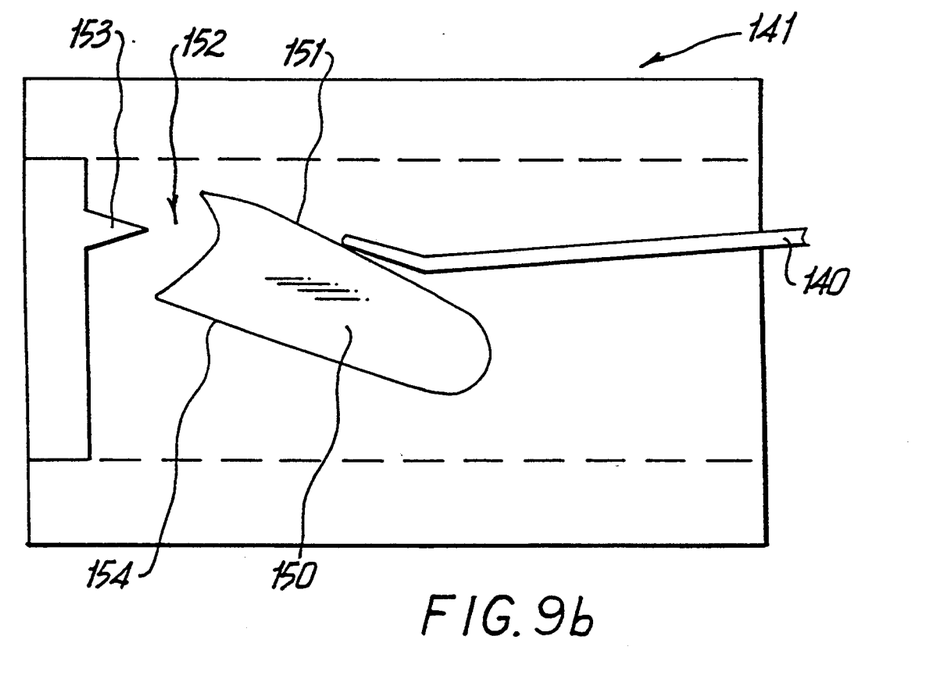
Figure 9C:
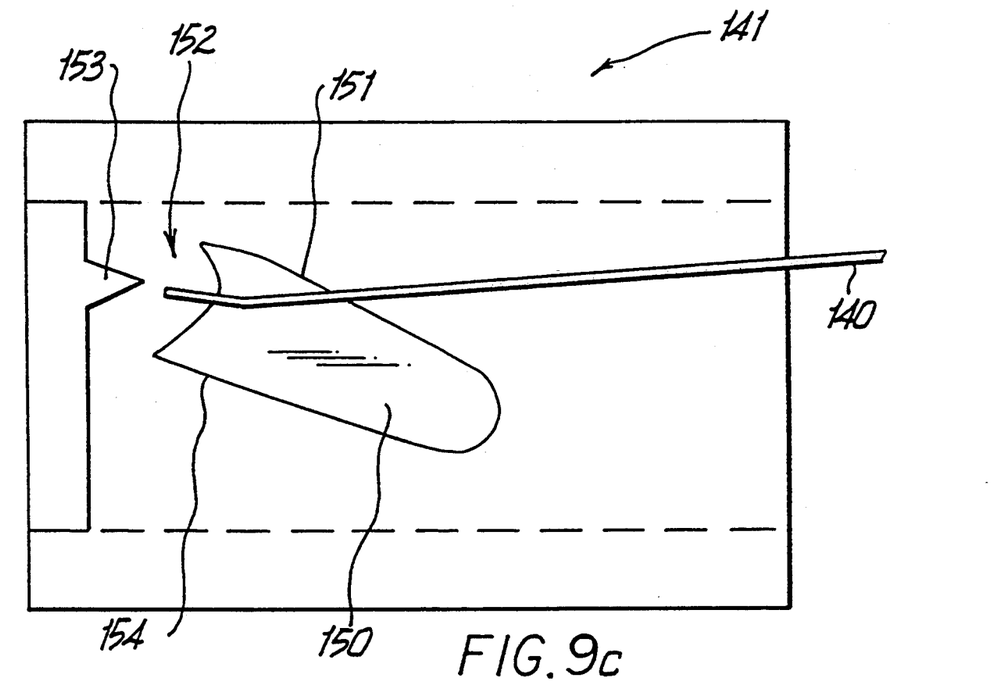
Figure 9D:
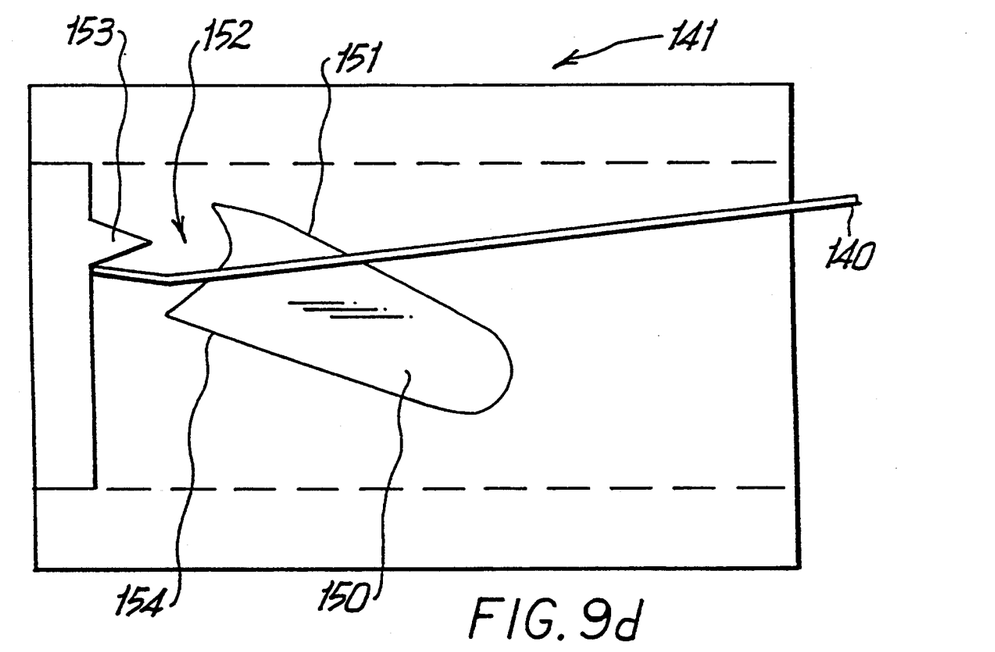
Figure 9E:
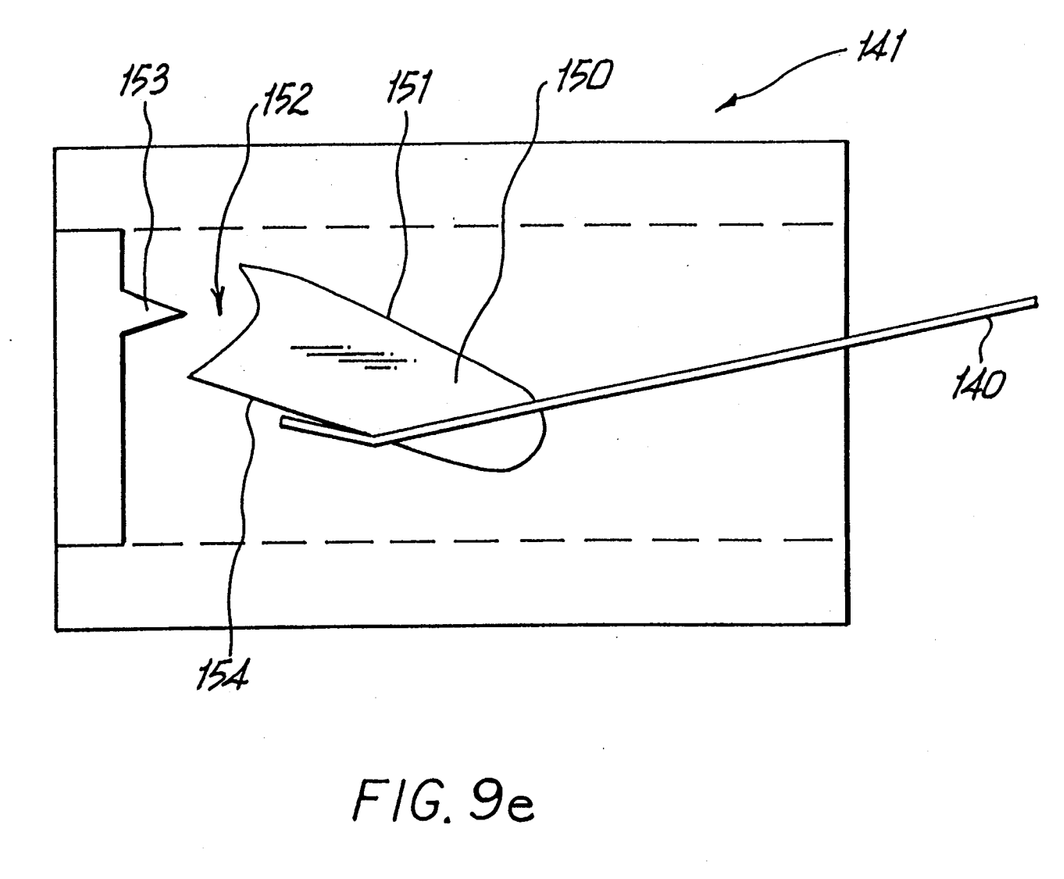
Figure 10:
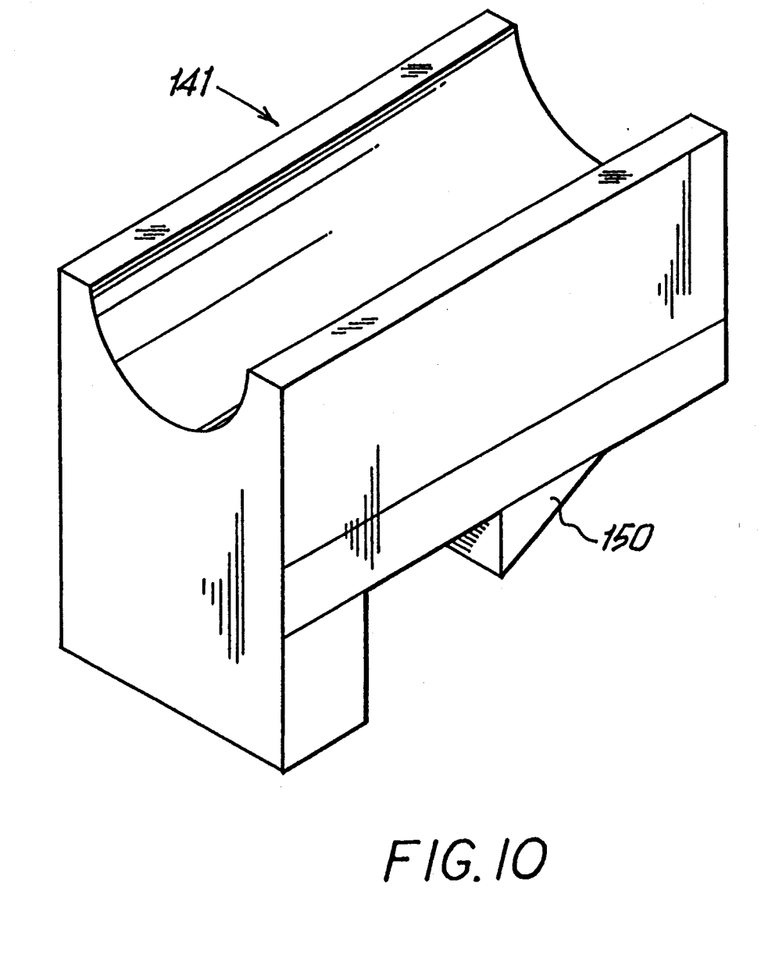
FIG. 10 illustrates a perspective view of the locking mechanism and release spring of the embodiment shown in FIG. 8.
Figure 11:
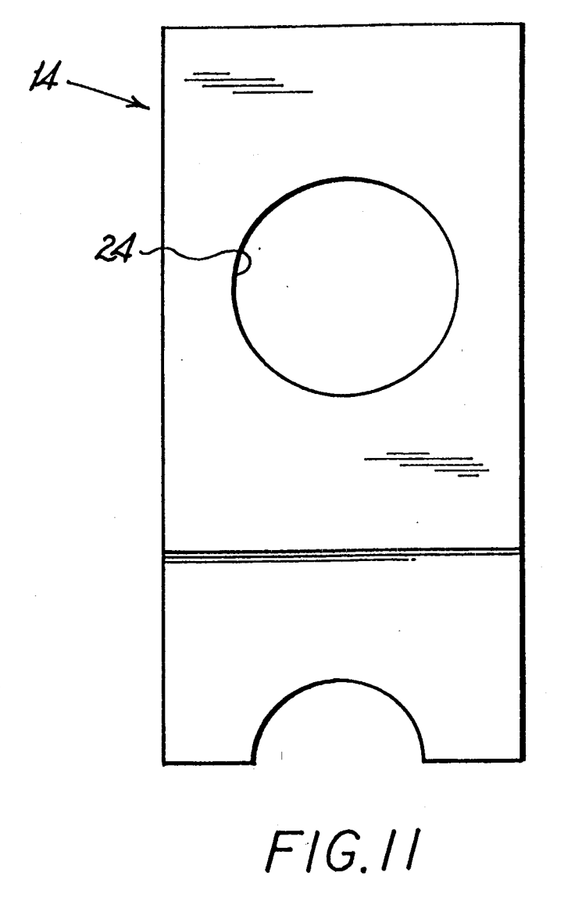
FIG. 11 illustrates a plan view of the brake member of the locking mechanism of the present invention.

The instrument of the present invention may be used for electrocautery purposes in addition to its cutting and grasping features. In this regard, as seen in FIG. 8, a coating 123 for insulation purposes may be provided over outer tube 119.

The insulation coating is necessary to avoid damage to surrounding tissue, thus providing the electrocautery feature at only the jaw mechanism. The insulation coating must conform to the shape of the body assembly to allow for smooth passage of the instrument through a cannula of a trocar to the surgical site, without snagging or abrading. Damage to the insulation coating may lead to an electrical path from the instrument to the cannula (typically constructed of a metallic material), thus damaging the surrounding tissue and exposing the surgical team to an electrical shock hazard. Therefore, the insulation must maintain its integrity during use and be resistant to abrasion. Furthermore, it must be uniform in thickness about the instrument to eliminate friction or abrasion as the instrument passes through a trocar assembly in a smooth and unobstructed manner.

In this regard, while heat shrink tubing, and coatings such as PFTE (Teflon), urethane and epoxies may provide'suitable insulation for the surgical instrument having an electrocautery feature, in the preferred embodiment of the present invention the body assembly is coated with a polymer such as diparaxylylene, which is a completely linear and highly crystalline material, manufactured by Union Carbide Corporation and known as parylene. Parylene provides a pin-hole free coating which is biocompatible and completely conforms to the shape of the instrument in a uniform manner. Parylene is applied in a vapor-deposition process in a vacuum chamber. During the application of parylene, the parylene layer builds uniformly with equal thickness on the entire surface of the instrument.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An endoscopic or laparoscopic surgical instrument comprising:
   a handle assembly including a barrel portion, a stationary handle, and a pivoting handle;
   a body assembly having a pair of coaxial members attached at one end to said handle assembly, including an inner rod member slidable within an outer tube member in response to movement of said pivoting handle of said handle assembly, said body assembly terminating at an end remote from said handle assembly at which end is provided a reciprocatingly movable tool mechanism; and
   locking means positioned within said barrel portion of said handle assembly including a locking block and a latch member selectively engagable and disengagable with said locking block to lock said tool mechanism, said locking means being actuable independent of the movement of said pivoting handle.

2. A surgical instrument according to claim 1, wherein said locking means further includes a pivoting braking means for frictionally engaging said inner rod member and a trigger mechanism for activating and deactivating said braking means.

3. An endoscopic or laparoscopic surgical instrument comprising:
   a handle assembly including a barrel portion, a stationary handle, and a pivoting handle;
   a body assembly having a pair of coaxial members attached at one end to said handle assembly, including an inner rod member slidable within an outer tube member in response to movement of said pivoting handle of said handle assembly, said body assembly terminating at an end remote from said handle assembly at which end is provided a reciprocatingly movable tool mechanism; and
   locking means positioned within said barrel portion of said handle assembly including a locking block and a latch member selectively engagable and disengagable with said locking block to lock said tool mechanism, said locking means further including braking means for selectively engaging said inner rod member, said locking means being actuable independent of the movement of said pivoting handle.

4. A surgical instrument according to claim 3, wherein said locking means further includes a trigger mechanism for activating and deactivating said braking means.

5. An endoscopic or laparoscopic surgical instrument comprising:
 a handle assembly including a barrel portion, a stationary handle, and a pivoting handle for incrementally opening and closing a tool mechanism;
 a body assembly extending from said handle assembly and including an inner rod member coaxially disposed within an outer tube member, said inner rod member reciprocatingly slidable within said outer tube in response to movement of said pivoting handle, said body assembly terminating at an end remote from said handle assembly at which end is provided a reciprocatingly movable tool mechanism; and
 a locking mechanism positioned within said barrel portion of said handle assembly for selectively locking said tool mechanism, said locking mechanism including braking means for engaging said inner rod member, a spring biased trigger member for controlling said braking means, and a latch member cooperatively associated with said trigger member for selectively latching said trigger member.

6. A surgical instrument according to claim 5, wherein said brake means includes an aperture through which said inner rod passes, said aperture being concentrically aligned with said inner rod when said locking mechanism is disengaged and eccentric in relation to said inner rod to frictionally engage said rod member when said locking mechanism is engaged.

7. A surgical instrument according to claim 5, wherein said trigger member pivots said braking means into engagement with said inner rod member, said trigger member being movable a first distance in a first direction to lock a position of said tool mechanism, and further being movable a second distance in said first direction to release said tool mechanism.

8. A surgical instrument according to claim 5, wherein said braking means is spring biased to an engaged position with said inner rod member, said trigger means being biased to maintain said braking means in a disengaged position.

9. A surgical instrument according to claim 5, wherein said braking means locks said inner rod member through frictional engagement of said braking means and said inner rod member when said locking mechanism is engaged.

10. A surgical instrument according to claim 5, wherein said trigger member includes a camming surface for engaging said latch member, said braking means pivoting out of engagement with said inner rod when said latch member is out of engagement with said camming surface, and said latch member locking said braking means in frictional engagement with said inner rod when said camming surface is engaged with said latch member.

11. A surgical instrument according to claim 5, further comprising electrical insulating means and electrocautery port means.

12. An endoscopic or laparoscopic surgical instrument comprising:
 a handle assembly including a barrel portion, a stationary handle, and a pivoting handle;
 a body assembly having a pair of coaxial members attached at one end to said handle assembly, including an inner rod member slidable within an outer tube member in response to actuation of said pivoting handle, said body assembly terminating at an end remote from said handle assembly at which end is provided a reciprocatingly movable tool mechanism; and
 a locking mechanism positioned within said barrel portion of said handle assembly, said locking mechanism including a locking block secured to said inner rod member and having a camming surface, said locking mechanism further including a latch member selectively engagable with said camming surface of said locking block for selectively locking said tool mechanism upon actuation of said pivoting handle;
 wherein said locking block is movable a first distance in a first direction to engage said latch member with said camming surface, and is movable a second distance in said first direction to disengage said latch member from said camming surface.

13. A surgical instrument according to claim 12, wherein said pivoting handle activates said inner rod member, such that manipulation of said pivoting handle slidingly reciprocates said inner rod member within said outer tube member.

14. A surgical instrument according to claim 12, wherein said inner rod member is free to move within said outer tube member when said latch member is out of engagement with said camming surface, and said latch member locking said inner rod when said latch member engages a notch on said camming surface.

15. A surgical instrument according to claim 14, wherein said inner rod comprises a pair of rod members joined by sliding joint means, said joint means allowing movement of one of said rod members while a second rod member remains stationary to permit disengagement of said locking mechanism.

16. A surgical instrument according to claim 12, further comprising electrical insulating means and electrocautery port means.

17. In combination, a handle assembly and a body assembly for endoscopic and laparoscopic surgical instruments, said body assembly being secured to said handle assembly at a proximal end of said body assembly and having a reciprocatingly openable and closable tool mechanism secured at a distal end of said body assembly;
 said body assembly comprising:
  a) an outer tube member,
  b) an inner rod member coaxially slidable within said outer tube member; and
 said handle assembly comprising:
  a) a pivotable handle for actuation of said inner rod member;
  b) a stationary handle adjacent said pivotable handle;
  c) a barrel portion for receiving said body assembly; and
  d) a locking mechanism positioned within said barrel portion for engaging said inner rod member, said locking mechanism including a locking block and a latch member selectively engagable and disengagable with said locking block to selectively lock said tool mechanism in a plurality of positions, said locking mechanism further including a brake member which engages said inner rod member to lock said tool mechanism; such that movement of said inner rod member within said outer tube member a first distance in a first direction locks said locking mechanism, and movement of said inner rod member a second distance in said first direction releases said locking, mechanism.

18. The combination according to claim 17, wherein said locking block is secured to said inner rod member, said block having a camming surface upon which said latch member rides during movement through said first distance, said latch member engaging a notch in said camming surface to lock said tool mechanism.

19. The combination according to claim 18, wherein said block includes a release tab which contacts said latch member during movement through said second distance to disengage said latch member from said notch to release said tool mechanism.

20. The combination according to claim 17, wherein said brake member includes an aperture concentrically aligned with said inner rod member when said locking mechanism is disengaged, said aperture being eccentric with said inner rod member when said locking mechanism is engaged to frictionally engage said rod member.

21. The combination according to claim 17, further comprising a trigger member extending outside said barrel portion for actuating said locking mechanism.

22. A surgical instrument according to claim 17, wherein said surgical instrument further comprises an electrical insulating means and an electrocautery port means.

23. The combination according to claim 17 wherein said locking mechanism is actuable independent of movement of said pivotable handle.

* * * * *